United States Patent
Cazalbou (10) Patent No.: US 10,583,222 B2
(45) Date of Patent: *Mar. 10, 2020

(54) COMPOSITE BIOMATERIALS WITH IMPROVED BIOACTIVITY AND THEIR USE FOR BONE SUBSTITUTE

(71) Applicants: UNIVERSITE PAUL SABATIER TOULOUSE III, Toulous (FR); Centre national de la recherche scientifique, Paris (FR)

(72) Inventor: Sophie Cazalbou, Rebigue (FR)

(73) Assignees: CENTRE NATIONAL DE LA RECHERCHE SCIENTIFIQUE (C.N.R.S.), Paris (FR); UNIVERSITÉ PAUL SABATIER TOULOUSE III, Toulouse (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/380,410

(22) Filed: Dec. 15, 2016

(65) Prior Publication Data

US 2017/0165403 A1    Jun. 15, 2017

(30) Foreign Application Priority Data

Dec. 15, 2015  (EP) .................................. 15307013

(51) Int. Cl.
*A61L 27/02* (2006.01)
*A61L 27/14* (2006.01)
(Continued)

(52) U.S. Cl.
CPC .......... *A61L 27/46* (2013.01); *A61B 17/8802* (2013.01); *A61C 8/0006* (2013.01); *A61F 2/2846* (2013.01); *A61L 27/20* (2013.01); *A61L 27/26* (2013.01); *A61L 27/32* (2013.01); *A61L 27/34* (2013.01); *A61L 27/54* (2013.01); *A61L 27/56* (2013.01); *A61L 27/58* (2013.01); *C08J 9/008* (2013.01); *C08J 9/30* (2013.01); *A61L 2400/12* (2013.01); *A61L 2430/02* (2013.01); *A61L 2430/12* (2013.01);
(Continued)

(58) Field of Classification Search
CPC ..... A61F 2/2846; A61C 8/0006; A61L 27/20; A61L 27/26; A61L 27/32
See application file for complete search history.

(56) References Cited

U.S. PATENT DOCUMENTS 3,767,437 A    10/1973 Cruz, Jr.
10,195,306 B2 * 2/2019 Cazalbou ................ A61L 27/32
(Continued)

OTHER PUBLICATIONS

Dubnika et al. Functionalized hydroxyapatite scaffolds coated with sodium alginate and chitosan for controlled drug delivery. Proceedings of the Estonian Academy of Sciences, 2012, 61, 3, 193-199. (Year: 2012).*

(Continued)

*Primary Examiner* — Lakshmi S Channavajjala
(74) *Attorney, Agent, or Firm* — B. Aaron Schulman, Esq.; Stites & Harbison, PLLC (57) ABSTRACT

The present invention concerns composite biomaterials comprising ceramic and a biodegradable polymer gel, with improved bioactivity, their process of preparation and their use for orthopedics, dentistry or reconstructive surgery, in particular for use as a bone filler.

11 Claims, 1 Drawing Sheet

(51) Int. Cl.
| | |
|---|---|
| A61L 27/46 | (2006.01) |
| A61L 27/34 | (2006.01) |
| A61B 17/88 | (2006.01) |
| A61C 8/02 | (2006.01) |
| A61F 2/28 | (2006.01) |
| A61L 27/20 | (2006.01) |
| A61L 27/26 | (2006.01) |
| A61L 27/32 | (2006.01) |
| A61L 27/54 | (2006.01) |
| A61L 27/56 | (2006.01) |
| A61L 27/58 | (2006.01) |
| C08J 9/00 | (2006.01) |
| C08J 9/30 | (2006.01) |

(52) U.S. Cl.
CPC ........ *C08J 2203/06* (2013.01); *C08J 2205/02* (2013.01); *C08J 2207/10* (2013.01); *C08J 2301/08* (2013.01); *C08J 2301/28* (2013.01); *C08J 2367/04* (2013.01); *C08J 2389/06* (2013.01); *C08J 2439/06* (2013.01)

(56) References Cited

U.S. PATENT DOCUMENTS

2006/0257492 A1   11/2006   Wen et al.
2010/0256774 A1   10/2010   Wang et al.

OTHER PUBLICATIONS

Partap et al., Supercritical Carbon Dioxide in Water Emulsion-Templated Synthesis of Porous Calcium Alginate Hydrogels. Advanced Materials, 2006, 18, 501-504 (Year: 2006).*

European Search Report for EP 15307013, completed Sep. 30, 2016.

Zhao-Li Mou et al: "Preparation of porous PLGA/HA/collagen scaffolds with supercritical CO and application in osteoblast cell culture", Journal of Supercritical Fluids, PRA Press, US, vol. 58, No. 3, Jul. 4, 2011(Jul. 4, 2011), pp. 398-406, XP028277316, ISSN: 0896-8446, DOI: 10.1016/J.SUPFLU.2011.07.003 [retrieved on Jul. 8, 2011] * abstract * * p. 399, col. 1, paragraph 2 * p. 404, col. 1, paragraph 2—p. 405, col. 2, paragraph 1.

Agnieszka Kawska et al: "The Nucleation Mechanism of Fluorapatite-Collagen Composites: Ion Association and Motif Control by Collagen Proteins", Angewandte Chemie International Edition, vol. 47, No. 27, Jun. 23, 2008(Jun. 23, 2008), pp. 4982-4985, XP055275245, DE ISSN: 1433-7851, DOI: 10.1002/anie.200800908 * p. 4983, col. 1, paragraph 1 * * p. 4985, col. 1, paragraph 2—col. 1, paragraph 2.

Helene Autefage et al: "Adsorption and release of BMP-2 on nanocrystalline apatite-coated and uncoated hydroxyapatite/[beta]-tricalcium phosphate porous ceramics", Journal of Biomedical Materials Research. Part B: Applied Biomaterials, vol. 91B, No. 2, Nov. 1, 2009 (Nov. 1, 2009), pp. 706-715, XP055269475, US ISSN: 1552-4973, DOI: 10.1002/jbm.b.31447 * abstract * * p. 706, col. 1, paragraph 1—p. 707, col. 2, paragraph 1.

Duarte A R C et al: "Processing of novel bioactive polymeric matrixes for tissue engineering using supercritical fluid technology", Materials Science and Engineering C, Elsevier Science S.A, CH, vol. 29, No. 7, Aug. 31, 2009(Aug. 31, 2009), pp. 2110-2115, XP026446080, ISSN: 0928-4931 [retrieved on Apr. 19, 2009] * abstract * * figure 1 * * p. 2110, col. 2, paragraph 3* * p. 2114, col. 2, paragraph 2-4.

Roghayyeh Marefat Seyedlar et al: "Gelation behavior of in situ forming gels based on HPMC and biphasic calcium phosphate nanoparticles", Carbohydrate Polymers., vol. 99, Jan. 1, 2014(Jan. 1, 2014), pp. 257-263, XP055307015, GB ISSN: 0144-8617, DOI: 10.1016/j.carbpol.2013.07.078 * abstract * * p. 263, col. 1, paragraph 2.

Shona Pek Y et al: "The development of a nanocrystalline apatite reinforced crosslinked hyaluronic acid-tyramine composite as an injectable bone cement", Biomaterials, Elsevier Science Publishers BV., Barking, GB, vol. 30, No. 5, Feb. 1, 2009 (Feb. 1, 2009), pp. 822-828, XP025801475, ISSN: 0142-9612, DOI: 10.1016/J.Biomaterials.2008.10.053 [retrieved on Nov. 22, 2008] * abstract * * p. 823, col. 1, paragraph 2—col. 2, paragraph 3 * * p. 827, col. 2, paragraph 4.

Partial European Search Report for EP 15307013 completed Jun. 28, 2016.

* cited by examiner

COMPOSITE BIOMATERIALS WITH IMPROVED BIOACTIVITY AND THEIR USE FOR BONE SUBSTITUTE

The present invention concerns the field of biomaterials capable, upon implantation, to stop bleeding related to surgery, to promote the penetration of main actors that lead to bone repair (biological fluids, cells, proteins, nutriments . . . ), to ensure a controlled release (fast then extended) of bioactive species known to promote bone formation and/or prevent certain post-operative complications (infection, inflammation). These biomaterials are mainly used for orthopedics, dentistry or reconstructive surgery, and more particularly the field of bone filling materials.

The chemical composition of bone mineral is that of a carbonate containing apatite deficient in calcium ions and with a portion of the $PO_4$ groups substituted with $HPO_4$ and $CO_3$. Its chemical formula $Ca_{8.3}\square_{1.7}$ $(PO_4)_{4.3}(HPO_4)_{0.7}$ $(CO_3)_{1.0}(CO_3,OH)_{0.3}\square_{1.7}$.

Its poorly crystallized apatite structure and the presence on the surface of crystals of labile environments make it very reactive, allowing it to participate in many exchange reactions with the surrounding ions in the body environment.

Calcium phosphates are the main constituents of hard tissues such as bones and teeth. It is the reason why over 40 years, research in bone filling materials has focused on the development of synthetic biomaterials obtained from various calcium phosphates.

Hydroxyapatite (HA) has thus become the reference compound in the field of bone substitutes as its composition is close to that of bone minerals and as it is stable at high temperature. This is why the first ceramics used as bone substitute were only composed with hydroxyapatite.

However, such bone substitutes are obtained at high temperature (>1000° C.) and are very poorly soluble in the body environment, so that residues may still usually be found in the bone implantation sites several years after implantation.

Lately, improved ceramics have made use of tricalcium phosphate (TCP) in order to improve the resorption. Used alone or most often associated with hydroxyapatite, TCP accelerates resorption of the material and increases the local release of calcium and phosphate, so as to promote new bone formation on the surface of hydroxyapatite.

The use of shaping processes associating blowing agents and adapted heat treatments have also helped to make considerable progress in improving the porosity of biomaterials used for bone filling.

The ceramics used today have a chemical composition close to that of bone minerals and an interconnected macroporous architecture similar to that of cancellous bone. These materials have significant benefits and are widely used when it comes to fill a bone defect. Nevertheless, they involve some disadvantages, including the followings:

Hydroxyapatite and tricalcium phosphate have the following chemical formula: $Ca_{10}(PO_4)_6(OH)_2$ and $Ca_3(PO_4)_2$, respectively. They thus have a chemical composition close but still different from those of bone minerals.

In addition, when subjected to elevated temperatures, these two stoechiometric compounds have a crystalline structure completely crystallized and hence unreactive.

In terms of morphology, the ceramics are typically constituted by particles welded together during sintering.

From a macroscopic point of view, materials having an important macroporous network are generally obtained; some heat treatments may sometimes lead to a microporous network. From a microscopic point of view, the absence of nano-sized or sub-micron porosity hinders the adsorption of proteins and limits their osteoconductive and/or osteoinductive properties.

In particular, HA, TCP or HA/TCP mixtures have a very low specific surface area and are thus hardly able to adsorb or to associate active species (ions, molecules, proteins) capable of being released in staged way (rapid, moderate or prolonged release). Indeed, the presence of both micropores (with diameter lower than 10 μm) and nanopores plays an important role in the efficiency of reconstruction of these materials, particularly on their osteoconductive and/or osteoinductive properties [Habibovic et al. Journal of orthopaedic research, 2008, 1363-1370]. Due to their large size, the pores of the existing ceramics cannot welcome cells but can be used to their anchoring in the implant. It was also found that osteoblasts better adhered on nanoporous ceramics, whereas fibroblasts adhered less.

Polymer gels are widely used as drug delivery systems but their lack of mechanical properties does not allow their use as bone filling materials.

An objective of the invention is therefore to provide a macroporous calcium phosphate ceramic acting as a skeleton having a chemical composition similar to that of bone minerals, combined with a biodegradable gel, which has controllable release properties, so as to form a composite biomaterial. Depending of its absorption capacity, said biomaterial may be used to stop bleeding linked to the surgery and/or to promote the penetration of biological fluids and the main actors that lead to the mineralisation.

The present invention also proposes to modify the composite so obtained so as to provide a composite biomaterial whose morphology is that of cancellous bone and the chemical composition of the surface is that of bone mineral itself.

Such modification has been found possible by submitting said composite biomaterial to supercritical $CO_2$ in aqueous conditions.

According to a first object, the present invention thus concerns a composite biomaterial comprising:
a. a mineral component comprising a calcium phosphate ceramic, where said ceramic comprises:
   hydroxyapatite (HA); or
   tricalcium phosphate (TCP); or
   a mixture thereof in the form of biphasic calcium phosphate (BCP);
b. an organic component comprising a biodegradable polymer gel;
characterized in that said composite biomaterial comprises deposited nanocrystals of apatite and one or more optional bioactive components.

According to an embodiment, the composite biomaterial has a nanosized porosity.

A "calcium phosphate ceramic" as used therein refers to any material comprising calcium and phosphate phases that may be used for biological applications, such as for bone repair, including bone filling or bone substitute. It is also called "bioceramic" hereafter.

The ceramic materials in accordance with the invention are primarily calcium phosphate ceramics generally obtained at high temperatures, that can be dense or porous. According to a particular embodiment, they are macroporous.

They are most often composed of hydroxyapatite (HA), tricalcium phosphate (TCP) or a mixture of these two compounds in the form of biphasic calcium phosphate (BCP) but may also contain phases such as fluorapatite (FHA) and/or chloro-apatite (CLHA).

According to an embodiment, the calcium phosphate ceramic according to the invention is such that it comprises calcium phosphate in anyone of the following forms:

Monocalcium phosphate monohydrate (MCPM) (Ca($H_2PO_4$)$_2$.$H_2O$), Monocalcium phosphate anhydrous (MCPA) (Ca($H_2PO_4$)$_2$), Dicalcium phosphate anhydrous (DCPA) (CaHPO$_4$), Dicalcium phosphate dihydrate (DCPD) (CaHPO$_4$.2$H_2O$), Octacalcium phosphate (OCP) (Ca$_8$H$_2$(PO$_4$)$_6$.5$H_2O$), α-Tricalcium phosphate (α-TCP) (α-Ca$_3$(PO$_4$)$_2$), β-Tricalcium phosphate (β-TCP) (β-Ca$_3$(PO$_4$)$_2$), Amorphous calcium phosphate (ACP) (Ca$_3$(PO$_4$)$_2$), Hydroxyapatite (HA) (Ca$_{10}$(PO$_4$)$_6$(OH)$_2$), Tetracalcium phosphate (TTCP) (Ca$_4$(PO$_4$)$_2$O), as well as the deficient or ion-substituted calcium orthophosphates.

They may be available in form of particulates, blocks, cements and coatings. They can be porous or dense and bioresorbable, or not. According to an embodiment, ceramics may be bioceramics obtained by using high temperature (sintering, firing, plasma spray . . . ). For example, porous calcium phosphate ceramics may be obtained by sponge replication, direct foaming techniques, vacuum-assisted foaming of a ceramic suspension (VFC), or freeze casting. Ceramics of the invention may also be calcium phosphate coating of porous material obtained by various methods, such as plasma spray coating (but this process presents a very poor infiltration capacity of porous materials), as electrophoresis, biomimetic approaches employing SBF solutions, saturated solutions or equivalent as well as other methods conducing to calcium phosphate coating of porous materials and/or macroporous calcium phosphate coating.

Such ceramics may be prepared according to the methodologies described in the literature, or they may be commercially available, such as for example the ceramics sold under the following trade names:

MBCP™ (Biomatlante, France), Ceraform™ (Teknimed, France), Interpore200™, Interpore, Netherlands), CrossBone™ (Biotech International, France), Bongros™ (CGBio, Korea), Bicalphos™ (Medtronic Sofamor Danek, USA), Syncera™ (Oscotec, Korea), BoneMedik™ (MetaBiomed Co, Korea).

"Modified biomaterial" as used therein refers to a composite biomaterial including the ceramic and the gel, as defined above where its structure has been modified so as to include apatite nanocrystals, and potentially active carbonated nanocrystals, in particular when actives species are introduced into the gel.

Where the biomaterial does not comprise the modified structure according to the invention, it is herein called "unmodified"

"Structure" as used therein includes all surfaces and networks of the composite biomaterial which may be available to a fluid where said composite is immersed in such fluid. It includes both the outer surface delimiting the shape of the ceramic, as well as the inner surfaces, which in turn refer to the surfaces created by the pores of the ceramic, as well as those of the polymer and the inner networks, and are not necessarily visible from the outer shape of the biomaterial.

"Modified structure" refers to the structure of a composite biomaterial as defined above including nanocrystals of apatite and actives carbonated nanocrystals within its network or on its surface.

"Nanocrystals" as used therein refers to crystals having a (size) average diameter of strictly less than 1 μm.

Said nanocrystals are deposited or precipitate within the structure of the composite biomaterial.

"Deposited" as used therein refers to the way such nanocrystals are formed in situ within the structure of the ceramics. Said crystals are generally precipitated on and grown over the surface or within the networks of the ceramic. It does not refer to the deposition of crystals that are formed beforehand.

"Precipitate" as used therein refers to the way such nanocrystals are formed in situ within the structure of the composites. Said crystals are formed by the reaction between the ionic species (cation) introduced during the gel formation or in the additional solution used during $CO_2$ treatment (treatment solution) and carbonate ions during treatment by supercritical $CO_2$.

The deposition according to the invention allows a fine layer to be formed.

The layer formed by the deposited nanocrystals has a thickness generally smaller than 10 μm.

"Macroporous" as used therein refers to the morphology of the ceramic comprising pores of (size) average diameter equal or greater than 1 μm.

"Nanoporous" as used therein refers to the morphology of the ceramic comprising pores of (size) average diameter strictly smaller than 1 μm.

The apatite nanocrystals present within the structure of the ceramic may be in particular nanocrystals of carbonated apatite, that are highly reactive towards the body environment whereas nanocrystals present within the structure of the composite (mainly located within the polymer network) may be carbonated crystals allowing by their dissolution to provide the release of bioactive components so as to generate a specific therapeutic activity.

According to an embodiment, the nanocrsytals of apatite are precipitated and formed on the surface of the biomaterial.

Said biomaterial is unmodified when it is merely coated by crystals that are previously precipitated.

Said biomaterial is modified when its surface is at least partly dissolved to form calcium and phosphate ions that are then reprecipitated in situ to form apatite nanocrystals that are deposited on the biomaterial and grow over its surface.

According to an embodiment the biodegradable polymer may be chosen from proteins, polysaccharides, aliphatic polyesters, and mixtures thereof.

According to a further embodiment, the polymer gel may be chosen in particular from collagen, gelatin, fibronectin, chitosan, hyaluronic acid, alginate, cellulose, PVA, PVP dextran, pullulan, poly (α-hydroxy acid) PLA, poly (glycolic acid) PGA, their PLGA copolymers, poly (ε-caprolactone) PCL, poly(3-hydroxybutyrate) PHB, poly(3-hydroxyalcanoate) PHA, their derivatives and mixtures thereof.

Derivatives include derivatives of cellulose such as CMC (carboxymethylcellulose), MC (methylcellulose), HPMC (hydroxypropylmethylcellulose), such as metolose, HPC (hydroxypropylcellulose).

According to a further embodiment, the polymer gel present within the composite biomaterial may be structured after the composite biomaterial is formed.

"Structured" or "structuration" as used herein, refers to the treatment of the gel so as to dry it and to form defined morphological properties, such as controlled porosity.

Generally, the gel is structured so as to create a macroporosity within the gel (ie pores of more than 1 μm of average diameter).

Typically, this may be achieved by known techniques, such as freezedrying or supercritical $CO_2$ drying.

The biodegrable polymer gels may be water soluble or not. It may be hydrophilic or not.

According to an embodiment, the gels are biodegradable hydrophilic polymers.

In particular, depending on the degree of hydrophilicity of the polymer used, the gel can be considered as cellular support and possesses at the same time the role of bioactive components reservoir, allows to control the phenomena of diffusion and the controlled release of the bioactive components, when polymer chosen is hydrophilic it promotes the penetration of biological fluids and of the main actors that lead to the mineralization (proteins, growth factors, nutrients, bone cells . . . ). It is advisable to choose a hydrophilic polymer which will allow stopping bleeding linked to the surgery, by way of its hydratation following implantation.

From a morphological point of view, the biomaterials of the invention having a modified structure have thus both an interconnected macroporosity that promotes cellular invasion and bone rehabilitation and a nanosized porosity which promotes protein adsorption and adhesion of osteoblasts responsible for bone formation, together with the capacity to controlled release bioactive components loaded within the composite biomaterial.

The physicochemical and morphological properties of the composite biomaterial of the invention may allow inter alliae:
An ability to promote the penetration of biological fluids and of the main actors that lead to the mineralization;
A prevention, or inhibition of local bleeding linked to the surgery;
A high reactivity and in particular a high capacity to react with the surrounding biological fluids;
A greater superficial resorbability with capacity to release locally more ions essential for new bone formation;
A greater adsorption capacity for different elements including proteins due to the presence of labile environments of apatitic nanocrystals located within the structure of the biomaterial and due to the presence of nanosized porosity;
An ability to promote cell adhesion and thus bone formation due to the nanosized porosity of the modified structure;
A controlled release of bioactive components loaded within the composite biomaterial.

According to an embodiment, the modified structure of the composite biomaterial of the invention may further comprise one or more additional bioactive components, chosen from bioactive ionic species and active ingredients.

"Bioactive" as used therein refers to the capacity of the composite biomaterials or the components thereof to interact with the biological environment where the biomaterial of the invention is implanted.

Said bioactivity may involve exchanges such as ion exchanges between the components of the modified structure and those of the bodily fluids, modifications of behavior of surrounding cells, and reactivity of the biomaterial with the surrounding biological fluids or tissues.

Bioactive components according to the invention include in particular ionic species such as $Mg^{2+}$, $Ag^+$, $Sr^{2+}$, $Zn^{2+}$, $Cu^{2+}$, $Ca^{2+}$, $Se^{2-}$, $Se^{4-}$.

These elements are progressively released by the modified structure by ionic exchange with the ions contained in biological fluids or tissues or during the resorption of the ceramic. When these elements are incorporated into labile environments of apatitic nanocrystals, their release may occur by simple exchange with the ionic species contained in the surrounding fluids (rapid release). When they are integrated in the crystalline structure of apatite nanocrystals or phases that constitute the ceramic, their release may occur due to the dissolution or resorption of the apatitic phases (slow and sustained release). When they are contained in carbonated nanocrystals (formed during supercritical $CO_2$ treatment) their release may be linked to the dissolution of said crystals (dissolution rate depending of the solubility of the said crystals). Depending on the selected ion species, it is possible to promote bone formation by stimulating osteoblast activity (Mg, Sr) and/or reduce the risk of infection (Zn, Ag, Cu . . . ) and/or inflammation (Zn).

Bioactive components also include active substances such as drugs that may be incorporated within the modified structure.

The morphology of the composite biomaterial may also be defined as bioactive, where the nanoporosity enhances the exchanges from and the reactivity of the surface components with the surrounding biological fluids or tissues where it is implanted.

The composite biomaterial of the invention may be useful for orthopedics, dentistry or reconstructive surgery.

According to a second object, the present invention provides for the use of the composite biomaterial of the invention for orthopedics, dentistry or reconstructive surgery.

According to a third object, the present invention concerns a bone repair material comprising the composite biomaterial according to the invention.

"Bone repair" as used therein refers to bone substitution or bone filling.

According to a fourth object, the present invention concerns a metal implant, such as a prosthesis coated with a composite biomaterial according to the present invention.

According to a fifth object, the present invention also concerns the use of a composite biomaterial of the invention for controlled release of bioactive components.

According to a sixth object, the present invention also concerns a process for preparing the composite biomaterial according to the invention.

Accordingly, said process for preparing the composite biomaterial comprises:
i. Mixing said calcium phosphate ceramic with said biodegradable polymer gel; and
ii. Reacting said mixture with supercritical $CO_2$.

$CO_2$ in the supercritical state is commonly used in the field of organic biomaterial since it allows maintaining their three-dimensional structure during drying. However, it has never been used as the reactional medium of the mineral phases. According to the present invention, the $CO_2$ in the supercritical state unexpectedly allows to modify the chemical composition of the ceramics to obtain the same composition as that of bone mineral and allows to precipitate active carbonated nanocrystals within polymer network.

According to the present invention, it may be used both as a drying method, sterilization and as reactional medium because it allows on one hand to modify the chemical composition of the sintered ceramics to obtain the same composition as that of bone mineral and on the other hand to precipitate "active" nanocrystals from the ionic species introduced inside the gel and/or inside the treatment solution.

According to an embodiment, the process comprises prior to step i the preliminary step of preparing the gel by mixing the polymer with a solution. Said solution may be chosen from an aqueous solution, one or more organic solvent, or mixtures thereof.

When the polymer gel is not soluble or not miscible in water or more generally is hydrophobic, the mixing step may generally be conducted in the presence of an organic solvent.

Said organic solvent is generally selected from solvents which allow the total dissolution of polymer and which is miscible with $CO_2$.

Suitable organic solvents include acetone, methanol, ethanol, chloroform, hexane, dimethyl sulfoxide.

A coarse emulsion may also be achieved by introducing a fraction of aqueous phase in the organic solvent described above. When the polymer gel is water-soluble or hydrophilic, the solution used to form the gel may be aqueous or may contain a fraction of an organic solvent miscible with $CO_2$. Adding an organic solvent miscible in $CO_2$ favours the drying of the composite.

The polymer gel used in step i may be loaded with bioactive components as defined above.

This may be achieved by mixing the obtained gel with an aqueous solution comprising said bioactive components, or alternatively preparing in one step a polymer gel loaded with bioactive components by mixing the polymer, with the aqueous solution comprising said bioactive components. As described above, various ions known for their biological activity may be introduced as bioactive components into the aqueous solution used to form the gel of the composite. Bioactive ionic elements which can be used are for example $Ca^{2+}$, $Mg^{2+}$, $Sr^{2+}$ (known to promote bone formation) and/or $Ag^+$, $Cu^{2+}$, $Se^{2-}$, $Se^{4+}$ (known for their bactericidal activity) and/or $Zn^{2+}$ (known for its antibacterial and anti-inflammatory activities). Some drugs can also be used to increase therapeutic efficacy and broad the spectre of activity of the material.

Once the gel is obtained, the mixing with the ceramic in step i can be carried out, e.g. by immersing the ceramic with the gel. The polymer gel optionally loaded with active elements may then be inserted inside the porous network of the ceramic skeleton by various methods, such as vacuum impregnation.

When a polymer insoluble in water is used, it is recommended, before performing $CO_2$ treatment of step ii, to remove the organic solvent by exchange with $CO_2$. Removing the organic solvent allows creating and stabilizing the tri-dimensional polymer network with interconnected porosity. The use of a coarse emulsion allows the filling of the previously porous network formed by an aqueous solution which promotes $CO_2$ treatment. In this case, as previously, it is recommended to perform the $CO_2$ treatment introducing composites in an aqueous or a mixed aqueous-organic solvent solution which can be consider as treatment solution.

Therefore, according to an embodiment, the process, where an organic solvent is used, comprises the step of removing said organic solvent, before conducting step ii.

Step ii is conducted by subjecting the mixture to supercritical $CO_2$. Generally, this reaction is conducted in the presence of an aqueous solution.

Said aqueous solution may be that present in the gel coming from the preparation of the gel, and/or may be added to step ii in the form of an extra aqueous solution (treatment solution).

According to an embodiment, the aqueous solution present may come from the polymer gel of step i and step ii may be conducted without adding an extra aqueous solution.

According to another embodiment, the aqueous solution present may be added for step ii in the form of an extra aqueous solution (treatment solution).

The treatment solution may be water, an aqueous solution, and may mixed with one or more organic solvent so as to form a solution or an emulsion if the solvent is not miscible in water. It may be the same solution used to form the gel, or the latter supplemented with calcium and phosphate ions dissolved, and/or can contain active ions or drugs.

The treatment solution may be water optionally comprising bioactive components as defined above, such as drugs, ionic species (as Mg, Ag, Sr, Zn, Cu . . . ), or calcium or phosphate species, or can be simulated body fluid (SBF). SBF is a solution with an ion concentration close to that of human blood plasma.

The composite biomaterial may be immersed or in contact with a humid environment (e.g. a wet gauze) and placed in a reactor under supercritical $CO_2$ atmosphere.

According to an embodiment, the ceramics loaded with the gel may be placed in an enclosed hydrated environment such as a aqueous medium reactor or in the presence of a small amount of water, for example a gauze impregnated with the aqueous solution or ideally in a container which contains an aqueous solution.

Generally speaking, the amount of the aqueous solution should be sufficient to wet the whole surface of the ceramic but should not be too important as the ceramic may be otherwise damaged during the processing by partial dissolution. The amount of the treatment solution to be added depends on the quantity and the nature of the ceramic. It can be determined by the skilled person by involving its skills and/or usual experiments.

According to an embodiment, the amount of the aqueous solution present during step ii is such that the weight ratio of said solution (L) with respect to the ceramic (S) is comprised between 0.2 and 50.

Where the aqueous solution is water, the L/S ratio is generally comprised between 0.2 and 10, typically between 1 and 5.

In case where the aqueous solution is concentrated SBF solution or solution containing calcium and phosphate ions, the L/S ratio may be comprised between 20 and 50.

Generally, the more dilute the solution, the smaller L/S.

During the treatment, the water present in step ii generates a local acidic environment which favours phenomena of dissolution-reprecipitation to the surface of the ceramic. However, despite the presence of the gel which limits diffusion phenomena of the ionic species, the use of an important amount of liquid may hinder the precipitation phenomena by dispersing the ionic species (introduced into the gel or from the superficial dissolution of the ceramic). Ideally the amount of water is less than L/S=20 but the addition of ions dissolved (ideally including calcium and phosphate ions) may favour the local sursaturation and allows the use of more important amount of solution (max L/S=50). SBF (simulated body fluid), even below its metastable state can be used.

According to an embodiment, step ii may be carried out at a pressure comprised between 2 and 10 000 bar, generally not exceeding 200 bar, typically comprised between 60 and 150 bar.

According to an embodiment, step ii may be carried out at a temperature comprised between 20 and 400° C., generally not exceeding 100° C., typically comprised between 30 and 50° C.

Typically, a supercritical $CO_2$ atmosphere may be achieved at temperature greater than 31° C. and pressure greater than 73.8 bar.

The modification of the surface of the ceramics is obtained by treating the material in the presence of water in a reactor under supercritical $CO_2$ atmosphere.

During the treatment in a supercritical $CO_2$ atmosphere, the water surrounding the material becomes saturated with $CO_2$. The pH of the solution decreases until reach a pH value around 4.

According to an embodiment, the process of the invention is such that the reaction mixture is maintained at an acid pH, generally lower than 6, typically around 4.

The acidic pH has the effect to induce a partial and superficial dissolution of the ceramic material. The partial dissolution of the ceramic surface leads to the release of phosphate ion and its counter ion, such as calcium ion and to a local pH rise.

During treatment, the $CO_2$ content in the atmosphere (in a gaseous or supercritical state) saturates the aqueous solution with dissolved carbonate ions thus decreasing its pH. The acidity of the aqueous solution caused by the dissolution of carbonate ions causes a superficial dissolution of the material.

Release of calcium and phosphate ions during superficial dissolution leads a local sursaturation in calcium and phosphate ions, which causes the precipitation of biomimetic carbonated apatite nanocrystals. The apatitic structure of calcium phosphates being considered as very tolerant of ionic substitutions, during the precipitation, some ionic species present in the aqueous environment of the material integrates apatitic structure of nanocrystals. This is the way the carbonates and $HPO_4^{2-}$ ions come to substitute themselves for the ions $PO_4^{3-}$ and $OH^-$. When no additional active element is added, the environment consisting of calcium, phosphates ($HPO_4$ and $PO_4$) and carbonates ($CO_2$, $HCO_3$, $CO_3$), the precipitated crystals are carbonated apatite nanocrystals similar to bone minerals. This species will be released slowly related to the resorption of the ceramic. In addition, when additional active elements are dispersed in the organic part of the composite, some of them integrate the labile environment as well as the crystalline structure of the new formed apatitic nanocrystals while others react with dissolved carbonate ions and cause the precipitation of bioactive carbonate nanocrystals. The release of ionic species are then function to their rate of dissolution.

Moreover the organization of newly formed apatite nanocrystals at the surface of the ceramic allows the creation of a porosity whose dimensions are significantly lower than that of the micron.

The resulting material has maintained its porous structure in a macroscopic scale but possesses from now a nanosized porosity (<1 μm) due to the precipitation of nanocrystals within the structure of the material, which have composition similar to those of bone mineral.

According to an embodiment, bioactive components can be added during the process either with the solutions or step i and/or step ii in order to provide a composite biomaterial with a therapeutic activity and/or allowing it to reduce post-operative complications (inflammation, infection).

Some drugs may also be added to the solutions in dissolved state or in suspension in order to be bound to the biomaterial and be released later in the body, once the material is implanted.

Bioactive components such as ionic species (as Mg, Ag, Sr, Zn, Cu . . . ) can be added to the solution(s) so as to introduce the apatitic structure of freshly precipitated nanocrystals.

Other ions such as calcium or phosphate may be added in order to promote the precipitation of the nanocrystals.

Other active substances such as drugs may be added to increase the therapeutic efficacy of the composite.

According to an embodiment, the process may comprise one or more further step chosen from:
drying the composite material; and/or
structuring the composite biomaterial;
where said drying/such structuration, may be carried out as defined above.

Once treatment is finished, the composites may be removed from the reactional mixture, dried. The gel may be structured to obtain a porous three-dimensional network with a sufficient size of pores to allow penetration of cells. The composites can be freeze-dried reactional mixture of step ii comprises, or can be dried in a supercritical $CO_2$ atmosphere.

If the reactional mixture of step ii comprises a significant amount of water (>25%), it is recommended to perform one or more washes in an organic solvent miscible with $CO_2$ before drying. This washing will help elimination of water contained in the gel by exchange with the organic phase and promote drying.

The solubility of water in $CO_2$ is very low (around 0.5% at 40° C. and 100 bar) but not negligible, the washing in an organic solvent can be avoided when the ratio water/$CO_2$ into the chamber remains very low (e.g. <5%).

For a $CO_2$ drying, composite biomaterial may be placed inside the supercritical $CO_2$ dryer. The chamber may be filled with $CO_2$ and then partially emptied 2-3 times in order to eliminate the organic solvent contained in the gel. The chamber may then be placed under supercritical conditions (T≤31.1 and P≤74 bars), left under these conditions for a certain time (minimum 15 minutes), then the pressure is generally decreased very slowly so as to return to atmospheric pressure. Depression parameters influence the size of the pores of the organic gel. The depression gradient may be adjusted depending on various parameters, such as the nature of the polymer gel, its viscosity . . . . This adjustment may generally be carried out by the skilled person by application and/or adaptation of known methods. Typically, to enhance the cells penetration, the depression may be adjusted so that the interconnected porosity may be comprised between 100 and 600 μm. Typically, to achieve a controlled release of the ionic species, the depression may be adjusted so that porosity may be below the micro range.

According to an embodiment, depressions may be carried out in sequence so as to create both types of porosity so as to increase both types of diffusion.

The process of the invention is thus a straightforward «green» process, which uses $CO_2$ in the supercritical state and can be easily implemented on the industrial scale to achieve ceramics with an improved bioactivity.

FIGURES

FIG. 1 (second line) was obtained with composites dried directly in $CO_2$ supercritical dryer after $CO_2$ supercritical treatment. FIG. 1 (third line) was obtained with the same composite than previous one but before drying in $CO_2$ supercritical dryer, it was immersed into ethanol (organic solvent miscible in $CO_2$) in order to eliminate water of the composite to exchange with ethanol and facilitate drying in supercritical conditions.

The following examples are given as a non-limiting illustration of the various objects of the invention.

Example 1: Composite BCP/PVP-CMC+Acetate Sr/No Treatment Solution/Washing with Ethanol Before $CO_2$ Drying Ceramic cubes with dimension 3 mm*3 mm*3 mm (0.408 g) consist in 65% hydroxyapatite (HA) and 35% tricalcium phosphate (TCP). Their total porosity is between 60 and 85% and the pore size is between 150 and 400 µm. A solution A is prepared from 2 g of strontium acetate dissolved in 100 ml of water.

The gel is formed using 0.05 g polyvinylpyrrolidone (PVP) and 0.2 g carboxymethylcellulose (CMC) in 20 ml of solution A.

Ceramics are introduced into the gel obtained. The gel is introduced into the porous ceramic network by subjecting the assembly (ceramics+gel) under vacuum and rapidly breaking the vacuum. The operation is performed 3 times. The composites obtained are removed from the gel.

Due to the fact that composites contain a large amount of water, they are directly placed in a chamber of a supercritical $CO_2$ dryer. The chamber temperature is raised to a temperature of 5° C. and then the chamber is filled in ⅔ full with liquid $CO_2$.

The temperature of the chamber is gradually increased to 50° C. and the pressure adjusted to 100 bar.

After 30 hours of treatment, the pressure is reduced very slowly (more than 60 minutes) to atmospheric pressure and the assembly is removed from the enclosure. In order to eliminate the water contained into the composites, they are introduced into absolute ethanol during 20 minutes. This operation is realized 2 times. The composites are then placed into the reactor enclosure of the $CO_2$ dryer. The chamber temperature is raised to a temperature of 5° C. and then the chamber is filled in ⅔ full with liquid $CO_2$. The enclosure chamber is filled and partially emptied 2 times. Then, the chamber is filled in ⅔ full with liquid $CO_2$ and the temperature is gradually increased to 35° C. and the pressure adjusted to 75 bar. After drying, the pressure is decreased very slowly (60 minutes to return to the atmospheric pressure).

Example 2: Composite BCP/HPMC/SBF0.9+Alcohol/No Treatment Solution/No Washing with Ethanol Before $CO_2$ Drying Ceramic cubes with dimension 3 mm*3 mm*3 mm (0.284 g) consist in 65% hydroxyapatite (HA) and 35% tricalcium phosphate (TCP). Their total porosity is between 60 and 85% and the pore size is between 150 and 400 µm. A solution A of SBF (0.9) (simulated body fluid with 0.9*the amount of traditionally used for SBF). A solution B is prepared by mixing 21 g of ethanol and 5 g of solution A.

A polymer gel is formed from 2 g of metolose 90SH-4000SR (HPMC from Shinetsu) and 25 g of solution B.

Ceramics are introduced into the gel obtained. The gel is introduced into the porous ceramic network by subjecting the assembly (ceramics+gel) under vacuum and rapidly breaking the vacuum. The operation is performed 3 times. The composites obtained are removed from the gel.

They are placed directly (in the absence of treatment solution) in a chamber of a supercritical $CO_2$ dryer. The chamber temperature is raised to a temperature of 5° C. and then the chamber is filled in ⅔ full with liquid $CO_2$. The temperature of the chamber is gradually increased to 50° C. and the pressure adjusted to 100 bar. After 24 h of treatment, the pressure is decreased very slowly (more than 60 minutes) to return to the atmospheric pressure and the temperature is also decrease to return to the room temperature. In order to dry the composites, the chamber temperature is raised to a temperature of 5° C. and then the chamber is filled in ⅔ full with liquid $CO_2$. The enclosure chamber is filled and partially emptied 2 times. Then, the chamber is filled in ⅔ full with liquid $CO_2$ and the temperature of the chamber is gradually increased to 35° C. and the pressure adjusted to 75 bar. After drying, the pressure is decreased very slowly (60 minutes to return to the atmospheric pressure). Results are illustrated in FIG. 1 (first and second line).

Figure 1:
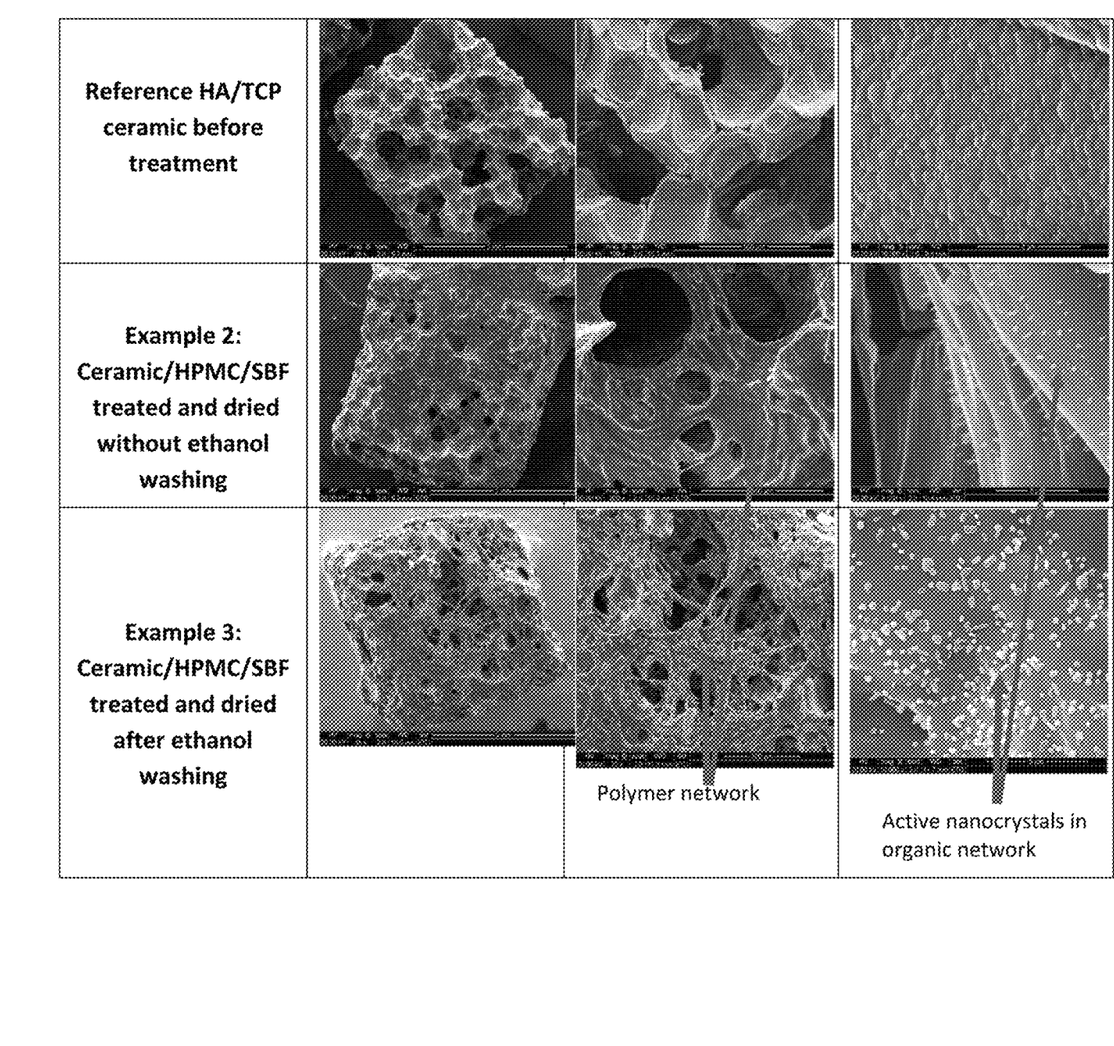
FIG. 1 illustrates the interconnected polymer and ceramic networks and the formation of the nanocrystals in the course of the process of preparation of the modified ceramics of the invention. Top of FIG. 1 shows the ceramic without gel before treatment.

The morphology of the composite is assessed by scanning electron microscopy (FIG. 1, second line) and compared to the ceramic (FIG. 1, first line).

The two first pictures illustrate firstly the modifications of porous network of the initial ceramic due to addition of polymer and secondly the organic porous network of interconnected pores of varying sizes.

The third picture highlights carbonated nanocrystals formed by precipitation during supercritical $CO_2$ treatment. These crystals formed after chemical reaction between carbonates and ionic species contained in SBF solution used to form the gel are located on the surface of polymer network as well as inside the polymer matrix forming a porous network.

Example 3: Composite BCP/Metolose/SBF0.9+Alcohol/No Treatment Solution/Washing with Ethanol Before $CO_2$ Drying Ceramics and gel are the same than those used in example 2.

The protocol used for performing the treatment is the same as used in Example 2.

After 24 h of treatment, the pressure is decreased very slowly (more than 60 minutes) to return to the atmospheric pressure and the temperature is also decrease to return to the room temperature.

The composites are removed from the enclosure chamber and immersed into absolute ethanol during 20 minutes. This operation is realized 2 times with fresh ethanol solution. The composites are then placed into the reactor enclosure of the $CO_2$ dryer. The chamber temperature is raised to a temperature of 5° C. and then the chamber is filled in ⅔ full with liquid $CO_2$. The enclosure chamber is filled and partially emptied 2 times. Then, the chamber is filled in ⅔ full with liquid $CO_2$ and the temperature of the chamber is gradually increased to 35° C. and the pressure adjusted to 75 bar.

After drying, the pressure is decreased very slowly (60 minutes to return to the atmospheric pressure). Results are illustrated in FIG. 1 (first and third line).

The morphology of the composite is assessed by scanning electron microscopy (FIG. 1, third line) and compared to the second line (Example 2) and the first line (the reference ceramic).

The two first pictures illustrate the modifications of porous network of the initial ceramic due to addition of polymer and the modifications of porous structure to the corresponding two first pictures of Example 2 due to the immersion of the treated composite into absolute ethanol before drying. It can be observe a more porous organic structure with pore sizes more important than those obtain in example 2 (composite without washing in ethanol).

The third picture of Example 3 highlights carbonated nanocrystals formed by precipitation during supercritical $CO_2$ treatment. These crystals formed after chemical reaction between carbonates and ionic species contained in SBF solution used to form the gel are located on the surface of polymer network as well as inside polymer matrix forming porous network.

Example 4: Composite BCP/Gelatin+$SrCl_2$/Treatment Solution: $SrCl_2$+SBF(0.9)/Washing with Ethanol Before $CO_2$ Drying Ceramic cubes with dimension 3 mm*3 mm*3 mm (0.293 g) consist in 65% hydroxyapatite (HA) and 35% tricalcium phosphate (TCP). Their total porosity is between 60 and 85% and the pore size is between 150 and 400 μm. A gelatin hydrogel containing: 3 g gelatin, 0.3 g $SrCl_2$ and 100 ml water is introduced as describe in previous examples into porous network of ceramics.

A solution A is prepared from 0.207 g $K_2HPO_4$, 0.2637 g $CaCl_2$, 3 g $SrCl_2$, 5.46 g TRIS buffer dissolved in 1l of deionised water. The pH is adjusted to 7.4 using HCl.

The composites are placed into a container with solution A. The amount of solution A used is that corresponding to L/S=2. The assembly is then placed in the chamber of a supercritical $CO_2$ dryer. The chamber temperature is raised to a temperature of 5° C. and then the chamber is filled in ⅔ full with liquid $CO_2$. The temperature of the chamber is gradually increased to 50° C. and the pressure adjusted to 100 bar. After 30 hours of treatment, the pressure is reduced to atmospheric pressure and the assembly is removed from the enclosure.

As in example 3, the composites are removed from the enclosure chamber and immersed into absolute ethanol during 20 minutes. This operation is realized 2 times with fresh ethanol solution. The composites are then placed into the reactor enclosure of the $CO_2$ dryer. The chamber temperature is raised to a temperature of 5° C. and then the chamber is filled in ⅔ full with liquid $CO_2$. The enclosure chamber is full and emptied 2 times. Then, the chamber is filled in ⅔ full with liquid $CO_2$ and the temperature of the chamber is gradually increased to 35° C. and the pressure adjusted to 75 bar.

After drying, the pressure is decreased very slowly (60 minutes to return to the atmospheric pressure). As previously described (in examples 2 and 3), the composites exhibit interconnected porosity as well as nanocrystals loaded within the polymer network.

Example 5: Composite TCP/(PLA+Chloroform)+ (SBF0.9+MgCl2+Water) Emulsion/No Treatment Solution/Washing with Acetone Before $CO_2$ Drying Ceramic cubes with dimension 3 mm*3 mm*3 mm (0.295 g) consist in 100% tricalcium phosphate (TCP). Their total porosity is between 60 and 85% and the pore size is between 150 and 400 μm.

Preparation of the organic phase: A solution A is prepared by dissolving 1 g of poly(d,l-lactic acid) (PURASORB PDL02A) in 3.45 g of chloroform. A solution B is prepared introducing 30 mg $MgCl_2$ in 100 ml of SBF(0.9) solution.

A coarse emulsion is prepared by mixing under stirring 2.7 g of solutions A and 2.1 g of solution B. The mixture is then introduced into the ceramic network as previously described under vacuum.

The composites are introduced in the chamber of supercritical dryer. The chamber is filled to two thirds with liquid $CO_2$. The composite is washed 2 times with liquid $CO_2$ to remove the chloroform and form the polymer network. A third filling is performed but this time, the chamber is raised to 45° C. and 100 bar in order to achieve the supercritical state of $CO_2$. The elimination of chloroform allows to form a polymer network filled with the aqueous solution (SBF+$MgCl_2$). The amount of water is sufficient (43.75% of the solvent constituting the emulsion with L/S=0.43): the treatment is carried out without additional treatment solution. The composites are maintained under these conditions for 5 hours and then the pressure and temperature are restored to the normal. When the processing is complete, the composites are removed from the chamber and then washed 2 times in an acetone solution. The washing with acetone allows to remove the water and promotes drying and structuration of three-dimensional network of polymer. Composites are introduced one last time inside the dryer to be dried using $CO_2$ in supercritical conditions (45° C.-100 b). The composites exhibit interconnected porosity and many apatite nanocrystals on the surface of the ceramic. The polymer, unlike the previous examples did not appear to have penetrated the entire network of porous ceramics and remains dispersed on the surface of the ceramic. It presents nanocristaux precipitated on its surface.

Example 6: Composite BCP/(PLA+Chloroform)+ (SBF0.9+MgCl2+Water) Emulsion/SBF+MgCl2+ Water Treatment Solution/Washing with Acetone Before CO2 Drying Ceramic cubes with dimension 3 mm*3 mm*3 mm (0.275 g) consist in 65% hydroxyapatite (HA) and 35% tricalcium phosphate (TCP). Their total porosity is between 60 and 85% and the pore size is between 150 and 400 μm.

Preparation of the organic phase: A solution A is prepared by dissolving 1 g of poly(d,l-lactic acid) (PURASORB PDL02A) in 3.45 g of chloroform. A solution B is prepared introducing 30 mg MgCl2 in 100 ml of SBF(0.9) solution.

A coarse emulsion is prepared by mixing under stirring 2.7 g of solutions A and 2.1 g of solution B. The mixture is then introduced into the ceramic network as previously under vacuum.

The composites are introduced in the chamber of supercritical dryer. The chamber is filled to two thirds with liquid $CO_2$. The composite is washed 2 times with liquid $CO_2$ to remove the chloroform and form the polymer network. A third filling is performed but this time, the chamber is raised to 45° C. and 100 bar in order to achieve the supercritical state of $CO_2$. The elimination of chloroform is used to form a polymer network filled with the aqueous solution (SBF+MgCl2).

The composites are placed into a container with solution B. The amount of solution B used is that corresponding to L/S=2. The assembly is then placed in the chamber of a supercritical $CO_2$ dryer. The chamber temperature is raised to a temperature of 5° C. and then the chamber is filled in ⅔ full with liquid $CO_2$. The temperature of the chamber is gradually increased to 45° C. and the pressure adjusted to 100 bar. After 30 hours of treatment, the pressure is reduced to atmospheric pressure and the assembly is removed from the enclosure.

When the processing is complete, the composites are removed from the chamber and from the treatment solution and then washed 2 times in an acetone solution. The washing with acetone allows to remove the water and promotes drying and structuration of three-dimensional network of polymer. Composites are introduced one last time inside the dryer to be dried using $CO_2$ in supercritical conditions (45° C.-100b). The result obtained is quite similar to those describe above, that is to say: the polymer remains positioned on the surface of the ceramic with the presence of precipitated nanocrystals. The ceramic has a large amount of apatite nanocrystals.

The invention claimed is:

1. A process for preparing a composite biomaterial with a nanosized porosity comprising:
   a. a mineral component comprising a calcium phosphate ceramic, wherein said ceramic comprises:
      hydroxyapatite (HA); or
      tricalcium phosphate (TCP); or
      a mixture thereof in the form of biphasic calcium phosphate (BCP); and
   b. an organic component comprising a biodegradable polymer gel;
   wherein said composite biomaterial comprises deposited or precipitated nanocrystals of apatite and one or more optional bioactive components, and
   wherein said process comprises
   i. mixing said calcium phosphate ceramic with said biodegradable polymer gel optionally loaded with said bioactive component, wherein said mixing is carried out in the presence of an aqueous solution and/or one or more organic solvents; and
   ii. reacting said mixture with supercritical $CO_2$.

2. The process according to claim 1, wherein the reacting is carried out at a pressure comprised between 2 and 10000 bar and a temperature comprised between 20 and 400° C.

3. The process according to claim 1, wherein the reacting is carried out at a pressure comprised between 60 and 150 bar and a temperature comprised between 30 and 50° C.

4. The process according to claim 1, wherein said mixing comprises vacuum impregnation.

5. The process according to claim 1 wherein said organic solvent is miscible in $CO_2$.

6. The process according to claim 1 wherein, where an organic solvent is used, the process further comprises removing said organic solvent before conducting the reacting.

7. The process according to claim 1, wherein step ii is conducted in the presence of an aqueous solution.

8. The process according to claim 7 wherein the aqueous solution present during the reacting comes from the biodegradable polymer gel or is added in the form of an extra aqueous solution (treatment solution).

9. The process of claim 7 wherein the amount of the aqueous solution present during the reacting is such that the weight (aqueous solution/ceramic) ratio (L/S ratio) is comprised between 0.2 and 50.

10. The process according to claim 7 wherein the aqueous solution is water optionally comprising bioactive components selected from the group consisting of bioactive ionic species and active ingredients.

11. The process according to claim 7, wherein said aqueous solution is simulated body fluid (SBF).

* * * * *